US005641510A

United States Patent [19]
Clark et al.

[11] Patent Number: 5,641,510
[45] Date of Patent: Jun. 24, 1997

[54] METHOD FOR TREATING CAPSULES USED FOR DRUG STORAGE

[75] Inventors: Andrew R. Clark, Half Moon Bay; Igor Gonda, San Francisco, both of Calif.

[73] Assignee: Genentech, Inc., South San Francisco, Calif.

[21] Appl. No.: 270,195

[22] Filed: Jul. 1, 1994

[51] Int. Cl.$^6$ ................................................ A61K 9/48
[52] U.S. Cl. ........................... 424/451; 424/452; 424/453; 424/456; 424/463; 424/46; 514/962
[58] Field of Search ............................ 424/45, 451, 452, 424/453, 46, 456, 463; 514/962

[56] References Cited

U.S. PATENT DOCUMENTS

| | | | |
|---|---|---|---|
| 3,173,840 | 3/1965 | Hostetler et al. | 106/122 |
| 4,500,358 | 2/1985 | Mayer et al. | 106/122 |
| 4,681,752 | 7/1987 | Melillo | 424/453 |
| 5,230,884 | 7/1993 | Evans et al. | 424/45 |
| 5,254,330 | 10/1993 | Ganderton et al. | 424/46 |

OTHER PUBLICATIONS

Ansel, H. C and Popovich, N. G. (1990). Pharmaceutical Dosage Forms and Drug Delivery Systems, Lea & Febiger, 5th edition, pp. 140–149.

Aitken et al., "Recombnant Human DNase Inhalation in Normal Subjects and Patients With Cystic Fibrosis" *JAMA* 267(14):1947–1951 (1992).

Hubbard et al., "Fate of Aerosolized Recombinant DNA–produced α1–antitrypsin: Use of the Epithelial Surface of the Lower Respiratory Tract to Administer Proteins of Therapeutic Importance" *PNAS USA* 86:680–684 (1989).

Hubbard et al., "A Preliminary Study of Aerosolized Recombinant Human Deoxyribonuclease I in the Treatment of Cystic Fibrosis" *The New England Journal of Medicine* 326(12):812–815 (1992).

Niemi, Jr., E.E., "Effects of Flow Resistance on the Correlation Between Theory and Experiment for the Performance of Cromolyn Sodium Inhalers" *Biomedical Sciences Instrumentation* 16:39–43 (1980).

Niven, R.W., "Aerodynamic Particle Size Testing Using a Time–of–Flight Aerosol Beam Spectrometer" *Pharm. Tech.* 17:72–82 (1993).

Okumura, K. et al., "Intratracheal Delivery of Calcitonin Dry Powder in Rats and Human Volunteers" *S.T.P. Pharma Sciences* 4(1):45–49 (1994).

Shak et al., "Recombinant Human DNase I Reduces the Viscosity of Cystic Fibrosis Sputum" *PNAS USA* 87:9188–9192 (1990).

Vidgren, M. et al., "Effect of Powder Inhaler Design on Drug Deposition in the Respiratory Tract" *International Journal of Pharmaceutics* 42:211–216 (1988).

Vogelmeier et al., "Aerosolization of recombinant SLPI to augment antineutrophil elastase protection of pulmonary epithelimium" *J. Appl. Physiol.* 69(5):1843–1848 (1990).

*Primary Examiner*—Raj Bawa
*Attorney, Agent, or Firm*—Wendy M. Lee

[57] ABSTRACT

Capsules (such as hard gelatin, cellulose and plastic capsules) containing pharmaceutical powders which are administered to a patient via inhalation are treated so as to increase the effective amount of the pharmaceutical agent reaching the respiratory system of the patient. The capsules are coated internally with a lubricant during manufacture and in one aspect, the method involves exposing the lubricant-coated inner surface of the capsule to a pharmaceutically acceptable solvent which dissolves the lubricant. Generally, the solvent is volatile, and bactericidal (e.g. ethanol). The pharmaceutical powder is inserted in the capsule following this washing procedure. Alternatively, the lubricant-coated capsule is dusted internally with a dusting agent such as a salt (e.g. sodium chloride) or a sugar (e.g. lactose, mannitol, trehalose or sucrose) prior to inserting the pharmaceutical powder inside the capsule. The invention also pertains to a capsule, optionally containing the pharmaceutical powder therein, which has been treated according to the methods discussed above.

17 Claims, 1 Drawing Sheet

METHOD FOR TREATING CAPSULES USED FOR DRUG STORAGE

BACKGROUND OF THE INVENTION

1. Field of the Invention

This invention is directed to capsules which are used as a storage medium for pharmaceutical powders. In particular, the invention pertains to a method of treating a hard capsule used to store a pharmaceutical powder wherein the powder requires delivery via inhalation, so as to enhance delivery of the pharmaceutical powder to the patient. The invention also relates to a hard capsule treated according to the above method.

2. Description of Related Art

Capsules are frequently used as a storage medium for finely divided pharmaceutical powders containing drug molecules requiring delivery via inhalation. The capsules consist of two halves that are separated, filled with the pharmaceutical powder and closed. Often, the capsule is a hard gelatin capsule, such as those referred to in Niemi, Jr. et al., *Biomedical Sciences Instrumentation* 16:39–43 (April 1980); Vidgren et al., *International Journal of Pharmaceutics* 42:211–216 (1988); Okumura et al., *S.T.P. Pharma Sciences* 4(1):45–49 (1994); U.S. Pat. Nos. 4,681,752; 3,173,840; and 4,500,358. Hard cellulose and plastic capsules suitable for storing pharmaceutical powders are also available commercially.

There has been an increase in the number of therapeutic proteins which have shown promise for administration by aerosol to the lungs of the patient for either local action or systemic absorption. For a review of these, see Niven R. W., *Pharm Tech.* 17:72–82 (1993).

For example, recombinant human deoxyribonuclease I (rhDNase) is administered as an aerosol to the lungs of patients suffering from cystic fibrosis. rhDNase is able to cleave DNA present in the thick, viscous secretions in the airways of the lungs of the patient thereby reducing sputum viscosity (see, e.g., Shaket al., *Proc. Nat. Acad. Sci.* 87:9188–92 [1990]; Aitken et al., *Jama* 267:1947–1951 [1992]; and Hubbard et al., *New. Eng. J. Med.* 326:812–815 [1992]).

Vogelmeier et al., *J. Appl. Physiol.* 69(5):1843–1848 (1990) and Hubbard et al., *Pro. Nat. Acad. Sci.* 86:680–684 (1989) discuss the neutrophil inhibitors; secretory leukoprotease inhibitor (SLPI) and alpha-1-antitrypsin, and their therapeutic potential when administered by aerosol via the respiratory route. U.S. Pat. No. 5,230,884 discloses an aerosol formulation for delivery of insulin to a patient's lungs.

Capsules containing drugs are generally used in conjunction with dry powder inhaler (DPI) devices such as the Spinhaler™, Rotahaler™ and Inhalator™. Prior to administration of the pharmaceutical powder, the capsules are cut or pierced so as to enable the pharmaceutical powder to be inhaled by the patient. Where the drug is to be delivered to the upper respiratory tract (i.e., intranasal), the drug particles generally need to be between about 20–100 μm in size. Where administration is to the lower respiratory tract (i.e., intrapulmonary), the drug particles generally need to be less than about 5 μm in size.

In order to improve the flow properties of the pharmaceutical powder (for ease of filling the capsules during manufacture and emptying the capsules during inhalation by the patients), the fine particles to be placed in the capsule can be "pelletized" into larger agglomerates or a physical blend of the finely divided drug powder with a carrier molecule can be made by mixing the powder containing the fine drug-containing particles with the coarser carrier. The carrier is typically lactose or mannitol and also acts as a bulking agent for low dose drugs. See, for example, U.S. Pat. No. 5,254,330. The fine drug containing particles adhere to the surface of the much larger carrier particles. Consequently, the total blend has the improved flow properties of the larger carrier particles.

Regardless of whether the drug is pelletized or attached to the carrier particle, it must become available again in the form of fine particles prior to entry into the patients' respiratory tract. This is typically achieved by spinning and shaking the capsule in the DPI and thereby breaking up the powder by various baffles and grids. The dispersed pharmaceutical compound is then inhaled into the lungs of the patient.

During the manufacture of capsules such as hard gelatin, cellulose and plastic capsules, their internal surfaces become coated in mould release lubricants. This is because the manufacturing process involves dipping mould pins into molten capsule-forming material, removing the pins and allowing the capsule-forming material to harden. The hard capsule shells are then removed from the pins. In order to remove the shells without damaging them, it is essential that the mould pins be lubricated. However, this lubricant tends to coat the inside surface of the capsule.

The inventors have discovered that this is problematic insofar as it reduces the effective amount of the pharmaceutical compound reaching the respiratory tract of the patient. For example, the inventors have found that formulations containing one milligram of recombinant human DNase can leave as much as 0.5 to 0.6 milligrams of recombinant human DNase adhering to the capsule walls. It was proposed that the retention of the drug in the capsule could be reduced using a lubricant composition considered to cause less adhesion. However, as demonstrated in Example 1 disclosed herein, capsule adhesion was not significantly reduced as a consequence of using an alternative lubricant composition.

Accordingly, it is an object of the present invention to overcome the problem associated with the retention of pharmaceutical powders to capsules, which problem was first recognized by the inventors of the present application. Overall, this method reduces drug loss as a consequence of administration by inhalation.

It is a further object of the invention to reduce the variation in the dosages of a pharmaceutical compound administered to different patients, particularly where the pharmaceutical compound is administered via inhalation at low dosages.

Other objects and advantages of the present invention will become apparent to one of ordinary skill in the art.

SUMMARY OF THE INVENTION

In accordance with the objects of the invention, a method of treating a lubricant-coated capsule which is used for storing a pharmaceutical powder is provided. The method involves exposing the lubricant-coated inner surface of the capsule to a specially selected solvent which dissolves the lubricant, prior to inserting the pharmaceutical powder in the capsule. Overall, this serves to improve aerosol delivery of the pharmaceutical powder to the patient. The solvent is a pharmaceutically acceptable solvent and is desirably bactericidal. The capsule is usually a hard gelatin, cellulose or plastic capsule.

In an alternative embodiment, the invention provides a method of treating a lubricant-coated capsule used for storing a pharmaceutical powder comprising dusting the lubricant-coated inner surface of the capsule with a pharmaceutically acceptable dusting agent prior to inserting the pharmaceutical powder inside the capsule.

The invention also pertains to a capsule treated according to either of the two preceding paragraphs. Usually, the treated capsule will have the pharmaceutical powder contained therein.

DETAILED DESCRIPTION OF THE PREFERRED EMBODIMENTS

Figure 1:
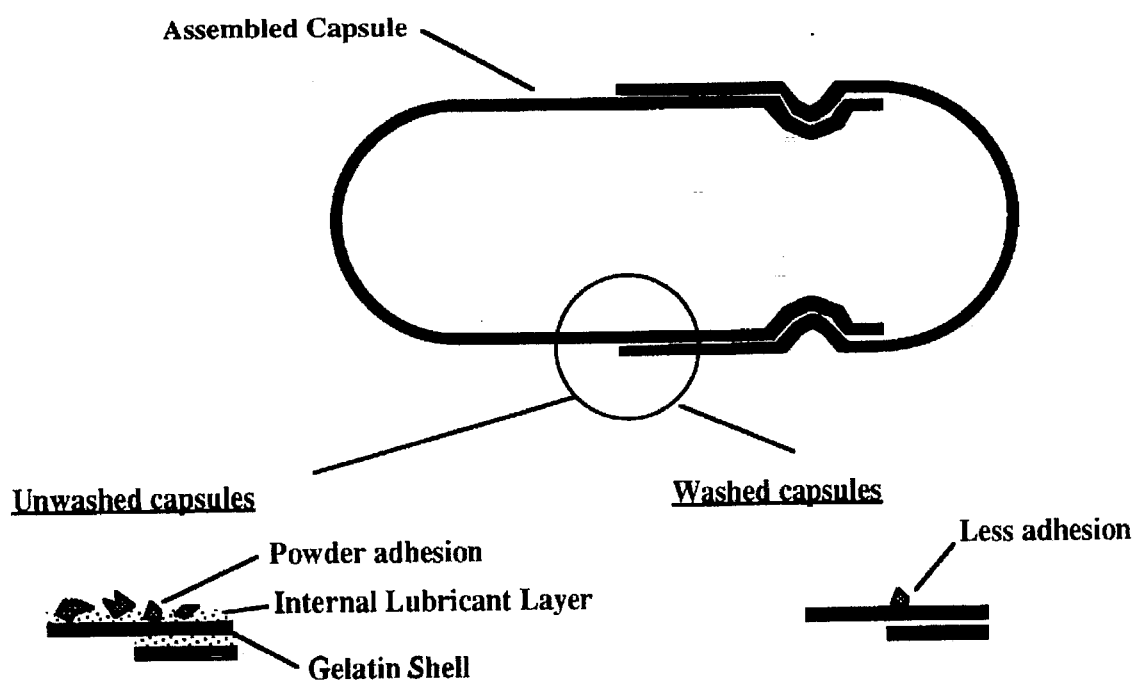
FIG. 1 is a transverse cross-section of a capsule used for storing a pharmaceutical powder which shows the layer of lubricant on the inner surface thereof and its removal. The degree of adhesion of the pharmaceutical powder for washed or unwashed capsules is illustrated.

Definitions:

The word "capsule" when used herein refers to a telescoping capsule having the characteristic shape shown in FIG. 1 and consists of two parts; a body and a cap of slightly larger diameter which fits snugly over its open end. The pharmaceutical powder is placed inside the space defined by the inside walls of the body and cap. The capsule is generally suitable for storing a pharmaceutical compound which is administered to the patient in the form of an aerosol. The capsule is "hard" which means that it is sufficiently rigid to enable the pharmaceutical powder to be stored therein, yet is able to be cut or pierced prior to use, to allow administration of the pharmaceutical powder to the patient.

Examples of suitable capsules include hard gelatin, cellulose and plastic capsules, which are made principally of gelatin blends, cellulose and plastic materials, respectively, but may contain dyes, opaquing agents, plasticizers and preservatives, for example.

U.S. Pat. Nos. 3,173,840 and 4,500,358 describe techniques for making hard gelatin capsules. Hard gelatin capsules can alternatively be purchased from Elanco Qualicaps, Inc. (Indianapolis, Ind.), for example. Alternatively, the capsule is formed from a plastic material, such as polycarbonate. Such hard plastic capsules can be purchased from Universal Plastics and Engineering Company, Rockville, Md., for example. The hard capsule can also be formed from cellulose, like those cellulose capsules sold by Torpac, East Hanover, N.J., for example.

It is possible to use capsules consisting of different materials, provided that they can be used to store a pharmaceutical product which is administered to a patient in the form of an aerosol.

The capsules are generally formed by dip-molding a film-forming solution. In the manufacture of such capsules, mould-release lubricants are used to facilitate removal of the mould pins from the capsule-forming core. Thus, a substantially uniform coating of the lubricant remains on the inside surface of the capsule halves.

By "lubricant" is meant a material capable of reducing friction between the mould pins and the inside surface of the formed capsule. The lubricant should be compatible with the capsule (i.e., should not degrade the capsule), should facilitate removal of the capsule from the mould pins and should be pharmaceutically acceptable (i.e., non-toxic). While the lubricant can be composed of a single lubricative compound, the lubricant will generally be a "lubricant composition" having one or more lubricative compounds and, optionally, other additives or diluents present therein.

Many suitable lubricants are available and can be selected by capsule manufacturers using routine experimentation. Examples of possible lubricants include: silicone oil; sodium or magnesium lauryl sulfate; fatty acids (e.g. stearic and lauric acid); stearates (e.g. magnesium, aluminum or calcium stearate); boric acid; vegetable oils; mineral oils (e.g. paraffin); phospholipids (e.g. lecithin); polyethylene glycols; sodium benzoate; and mixtures of the above. Often, other components are present in the lubricant. For example, calcium soap may be dispersed in the oil lubricant. Sometimes, the lubricant is dissolved in petroleum, for example. Such lubricant compositions are well known in the art and are encompassed by the term "lubricant" when used herein.

The term "pharmaceutically acceptable solvent" when used herein refers to a liquid which is able to dissolve the layer of lubricant on the inside surface of the capsule, but not the capsule. Any residual solvent remaining on the capsule following washing should not be reactive with the pharmaceutical powder, should not cause irritation of the respiratory tract of the patient and should otherwise be without other negative side-effects upon administration of the pharmaceutical powder to the patient.

By "dissolve" is meant the ability of the solvent to remove the lubricant coating from the inside surface of the capsule. Thus, the solvent is selected according to the nature of the lubricant present on the inside surface of the capsule. For example, if the capsule is coated with an oil, a water-miscible, volatile solvent such as alcohol (e.g. methanol, ethanol, propanol, isopropanol) can be used. Alcohol has the added advantage of being bactericidal and thereby provides a sterilization step in the production process. Other suitable solvents which can dissolve the lubricant coating on the inside surface of the capsule can be selected by those skilled in the art. For example, solvents which are not miscible with water, such as chloroform or carbon tetrachloride, can also be utilized. An aqueous soap or detergent solution can also be used.

Table 1 follows which lists exemplary lubricants and examples of suitable solvents for dissolving these lubricants:

TABLE 1

| Lubricant | Solvent |
| --- | --- |
| Silicone oil | Benzene, hexanol |
| Sodium or magnesium lauryl sulfate | Water |
| Fatty acids (e.g. stearic and lauric acid) | Alcohol, propylalcohol ether, benzene |
| Stearates (e.g. magnesium, aluminum or calcium stearate) | Warm alcohol |
| Boric acid | Water, water/alcohol mixtures |
| Vegetable oils | Alcohol, detergent solutions chloroform, carbon tetrachloride |
| Minerals oils (e.g. paraffin) | Benzene, ether, chloroform, carbon tetrachloride |
| Phospholipids (e.g. lecithin) | Alcohol, alcohol/water mixtures, ether |
| Polyethylene glycols | Alcohol, alcohol/water mixtures, ether |
| Sodium benzoate | Water, alcohol and their mixtures |

However, the above list of lubricants and solvents is, by no means, exhaustive. Selection of other suitable solvents to remove a particular lubricant is possible using no more than routine experimentation.

The term "pharmaceutical powder" when used throughout this application refers to a powder containing at least a pharmaceutical compound and, optionally, a pharmaceutically acceptable carrier or excipient. The pharmaceutical powder is generally administered to the respiratory tract of the patient in the form of an aerosol. Often, the pharmaceutical compound comprises a polypeptide. The invention is especially useful for low dosage drugs. However, other non-polypeptide pharmaceutical products are clearly within the scope of the invention claimed. The average size of the particles of the pharmaceutical powder containing the therapeutic agent is preferably in the range 0.1 to 20 micrometers, more preferably 1 to 6 micrometers. Typically, at least 50% of the particles will be of a size which falls within this range, although the presence of significant quantities of fine material is contemplated within the scope of the invention.

A "pharmaceutical polypeptide" refers generally to peptides and proteins having more than about ten amino acids. Examples of polypeptide pharmaceutical compounds include molecules such as alkaline phosphatase, β-lactamaserenin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombazine; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies such as anti-HER2 and anti-IgE; and fragments of any of the above-listed polypeptides.

The most preferred polypeptide is deoxyribonuclease (DNase), especially recombinant human DNase (rhDNase).

Examples of non-polypeptide pharmaceutical compounds which can be administered to the respiratory tract of a patient include agents with an anti-histamine and anti-allergic action such as sodium cromoglycate, beta-agonists, anticholinergics such as oxytropium bromide and thiazinamide chloride, sympathomimetic amines such as terbutaline, salbutamol, clenbuterol, pirbuterol, reproterol, procaterol and fenoterol, steroids especially corticosteroids such as beclomethasone dipropionate, and mucolytics such as ambroxol.

Examples of other pharmaceutical compounds which might usefully be incorporated into the hard gelatin capsule include hypnotics, sedatives, tranquilizers, anti-inflammatory agents, anti-histamines, anti-tussives, anti-convulsants, muscle-relaxants, anti-spasmodics, cardiovascular agents, anti-bacterials such as pentamidine, antibiotics and hypoglycemic agents.

Sometimes, the pharmaceutical powder includes a pharmaceutically acceptable carrier or excipient. For example, a physical blend of the pharmaceutical compound and the carrier can be made wherein the fine pharmaceutical particles adhere to the much larger carrier particle. Alternatively, a mixture of the pharmaceutical compound particles and the excipient can form the pharmaceutical powder. Examples of pharmaceutically acceptable carriers or excipients include, but are not limited to, salt compounds (e.g. sodium chloride) or sugar compounds (e.g. glucose, fructose, lactose, mannitol, trehalose and sucrose). The sugar compounds may be crystalline, amorphous or mixtures thereof.

Other compounds can be present in the pharmaceutical powder where required or desired. For example, a bronchodilator (e.g. isoprenaline, rimiterol, ephedrine, ibuterol, isoetharine, fenoterol, carbuterol, clinbuterol or pharmaceutically acceptable salts thereof) or a coloring or flavoring agent or preservatives such as those which are conventionally incorporated into dry powder inhalant compositions, may be present in the pharmaceutical powder.

The phrase "pharmaceutically acceptable dusting agent" refers to a compound which can be used to dust the inside of the lubricated capsules thereby adsorbing the lubricant on the surface of the capsules. It was found in the experiments disclosed herein that the dusting agent should be substantially "fine", having an average particle size of between about 0.1 to 20 micrometers, more preferably between about 0.5 to 10 micrometers, and most preferably between about 1 to 6 micrometers. Typically, about 50% of the particles of the dusting agent will be of a size which falls within the exemplified ranges, although the presence of significant quantities of fine material is tolerable. To achieve the desired particle size, the dusting agent may be micronized or spray dried, for example, using conventional techniques. It has been found that the pharmaceutical powder adheres to the pre-dusted capsules to a lesser extent than to the capsules without the layer of the dusting agent therein. The dusting agent is pharmaceutically acceptable and accordingly, the dusting agent should not be reactive with the pharmaceutical compound, should not cause irritation of the respiratory tract of the patient and should otherwise be without other negative side-effects upon administration of the pharmaceutical powder to the patient. Examples of dusting agents include monosaccharides (e.g. lactose, mannitol, arabinose, xylitol and dextrose and their monohydrates), disaccharides (e.g. maltose or sucrose) and polysaccharides (e.g. starches, dextrins or dextrans), salts (e.g. sodium chloride or potassium chloride), cellulose, methylcellulose or solid powders of polyethylene glycols and similar substances. Micronized crystalline sugars or spray dried amorphous sugars (such as glucose, fructose, mannitol, sucrose and especially micronized lactose) or micronized sodium chloride are preferred dusting agents.

MODES FOR CARRYING OUT THE INVENTION

The invention provides a method for treating capsules which are used for storing a pharmaceutical powder such as those described above. The capsule may be used in conjunction with any inhaler employing hard capsules, such as the following commercial inhalers Spinbaler™ (sold by Fisons, UK); the I.S.F. Inhaler (sold by I.S.F., Italy); Inhalator™ (sold by Boehringer-Ingelheim, Federal Republic of Germany); Rotahaler™ (sold by Glaxo, UK).

The hard gelatin capsules are made by dip-molding film forming gelatin solution and can be purchased commercially from Elanco Qualicaps, Inc., Indianapolis, Ind., for example. Hard plastic capsules can be purchased from Universal Plastics and Engineering Company, Rockville, Md., for example. The company Torpac of East Hanover, N.J., sells cellulose capsules which also fall within the scope of the instantly claimed invention. As discussed previously, during manufacture the capsules are coated with a lubricant to facilitate easy release of the capsule shell from the mould pin. Consequently, the interior of the capsules will be coated with the lubricant. See FIG. 1.

Accordingly, the capsule is placed in a suitable solvent so as to expose the layer of lubricant on the inside wall of the capsule to the solvent and thereby remove the solvent therefrom. Suitable solvents which are able to dissolve the lubricant have been mentioned above. If a different lubricant from those mentioned herein is used during manufacture of the capsule, a suitable solvent which is able to dissolve the lubricant can be selected via routine experimentation.

While absolute alcohol may be used for washing the hard gelatin capsule, the inventors have found that this may reduce the water content of the gelatin capsule, thus causing the capsule to become brittle. This may cause the hard gelatin capsule to shatter during use. Therefore, re-equilibrating the capsules at an appropriate relative humidity following washing in the solvent can replace lost water and hence return the capsules to the original water content and texture. Alternatively, alcohol containing a suitable proportion of a pharmaceutically acceptable aqueous diluent such as water (e.g., forming an alcohol composition having about 0 to 20% by weight water), rather than absolute alcohol can be used during the washing procedure such that the water content of the gelatin capsule remains constant during washing.

Following washing and drying, the pharmaceutical powder is placed inside the capsule and the capsule is closed using techniques which are well known in the art for such a procedure.

The pharmaceutical powder having the desired average particle size can be prepared by dry mixing the pharmaceutical compound and excipient or carrier (and optionally other components, such as a bronchodilator) and sieving the composition thus formed. If necessary, the pharmaceutical compound can be pelletized into larger agglomerates using standard techniques. Alternatively, the carrier molecules can be coated with the finer pharmaceutical particles using widely used milling techniques or other methods for preparation of fine powders, such as spray-drying.

The capsule is then used in the normal way so as to administer the pharmaceutical compound to the patient, usually via inhalation to the respiratory tract of the patient.

The invention also relates to a capsule treated according to the method disclosed above and, optionally, containing the pharmaceutical powder therein.

In an alternative embodiment, following manufacture, the lubricant-coated capsules are dusted with a dusting agent such as those exemplified above. The capsules are then filled with the pharmaceutical powder and used in the normal way. This dusting step causes the dusting agent to be adhered to the inside surface of the capsule. This reduces the amount of the pharmaceutical powder which is able to adhere to the inside surface of the capsule and thus increases the overall amount of the pharmaceutical compound reaching the respiratory tract of the patient.

The invention will be more fully understood by reference to the following examples. They should not, however, be construed as limiting the scope of the invention. All literature and patent citations are expressly incorporated herein by reference.

EXAMPLE 1

Lubricant Replacement

Lecithin, or a mixture of calcium soap dispersed in mineral oil together with a blend of polyethylene glycols (having various molecular weights), are generally employed by Elanco Qualicaps, Inc. as lubricants in their manufacture of hard gelatin capsules. The inventors recognized that drug delivery from hard capsules was not being optimized because significant amounts of the drug were remaining inside the gelatin capsules following simulated inhalation. The inventors discovered that this problem was due to the presence of a coating of the lubricant on the inside surface of the capsules. Accordingly, it was proposed that the lubricant normally used during manufacture of the capsules be replaced with an alternative blend, which was considered by the manufacturers to be less "adhesive", in order to overcome the problem. The conventional capsules are referred to herein as "standard" capsules. Capsules having the alternative blend of lubricant are termed "inhalation" capsules, since it was expected that these capsules would be better adapted for inhalation insofar as retention of the pharmaceutical powder to the inside surface of the capsule was concerned. The experimental procedure is discussed below.

A. rhDNase Powder Blends

Investigations were carried out using formulations containing spray dried powders of rhDNase with a lactose carrier as a flow aid and bulking agent. Manufacture of rhDNase is disclosed in Shak et al., *Proc. Nat. Acad. Sci.* 87:9188–9192 (1990). Spray dried powders of rhDNase are disclosed in U.S. patent application Ser. No. 08/206,020, filed Mar. 4, 1994. The formulations were designed to give capsules containing 1 mg of rhDNase with a 10 mg total fill weight. The spray dried powder was blended in a 1:9 ratio with "coarse" carrier lactose (DCL 11, Pharmatose, DMV Inc., La Crosse, Wis.).

Each blend was prepared using a combination of sieving and "tumbling" steps. The components of the blend were weighed directly onto the mesh of a 4 inch diameter 250 μm sieve. The mixture was sieved and then placed in a small glass bottle. The bottle was then "tumbled" using a standard laboratory roller for 5 minutes. The sieving and tumbling procedure was repeated 3 times before the blend was considered ready for use.

B. Multistage Impinger

A Multiple Stage Liquid Impinger (MSLI) was used to characterize the size distribution of the rhDNase aerosols generated from the rhDNase formulation. The MSLI is a three stage inertial impactor which incorporates an inlet bend, or "throat", designed to crudely represent the mouth and oropharynx of patients, and a terminal filter to capture all material passing the last impaction stage.

The apparatus was assembled and known quantities of Milli-Q water were pipetted into each stage chamber. The flow rate was adjusted appropriately using a Sierra Instruments mass flow meter (model no. 82152-H-3). Five individual pre-weighed, pre-pierced standard or inhalation capsules, containing a nominal dose of 1 mg of powdered rhDNase, were discharged from a dry powder inhaler (DPI) by placing the capsules into the DPI and then connecting the DPI to the impinger throat. After the last capsule was discharged into the MSLI, the pump was switched off. The MSLI was then agitated to ensure that the protein powder deposited on each stage was dissolved in the water contained in the stage chamber where it deposited. Aliquots of each solution were withdrawn and the protein concentration measured by UV spectroscopy at 280 nm. The capsule, device, throat and filter (Whatman No.1) were washed quantitatively with Milli-Q water and the protein content determined as above.

C. Results

Capsule retention, device retention, delivered dose and respirable dose for either the standard or inhalation capsules were quantified. The results are shown in the following table.

TABLE 2

Comparison of Standard and Inhalation Capsules

MSLI @ 60 liters per minute, mean of 10×10 mg capsules containing 1:9 blend formulation

| Capsule | Capsule Retention of rhDNase (mg) | Device Retention of rhDNase (mg) | Delivered Dose of rhDNase (mg) | Respirable Dose of rhDNase[1] (mg) | Respirable Percentage[2] (%) |
|---|---|---|---|---|---|
| Standard | 0.54 | 0.10 | 0.36 | 0.14 | 40 |
| Inhalation | 0.59 | 0.05 | 0.36 | 0.11 | 31 |

[1]. Respirable dose refers to the fraction of the nominal dose less than 6.3 μm in diameter. It is a measure of that fraction of the nominal dose with the potential to penetrate and be deposited in the lower airways.
[2]. Respirable percentage is the fraction of the delivered dose less than 6.3 μm in diameter. It is a measure of the "dispersibility" of the powder aerosol.

D. Conclusions

While it had been expected that use of the inhalation lubricant for manufacture of the capsules would reduce adhesion of the pharmaceutical powder to the inside of the capsule wall, it was found that no significant reduction in adhesion to the capsule was achieved. Accordingly, changing the lubricant used for manufacture of the hard gelatin capsules did not overcome the problem identified by the inventors (i.e, a reduction in the effective amount of the pharmaceutical compound reaching the respiratory tract of the patient as a consequence of adhesion to the inside of the capsules).

EXAMPLE 2

Solvent Washing

Capsule washing experiments were carried out using ethanol as an exemplary solvent. rhDNase blends, "standard" capsules, capsule emptying and multistage impinger were as described for Example 1.

A. Washing Procedure

Size 3HK "standard" hard gelatin capsules (Bx DOKZ30), supplied by Elanco Qualicaps, were used for the studies. Hole piercing was performed with a hot needle with a diameter of approximately 1.2 mm. The two halves of approximately 100 capsules were separated and placed in 200 ml of absolute ethanol. After stirring for approximately 2–3 mins, the ethanol was drained and the capsules were allowed to dry in air overnight. They were then stored overnight at 50% relative humidity to re-equilibrate.

B. Results

Table 2 below presents the emptying data obtained with ethanol washed and un-washed capsules. It can clearly be seen that pre-washing reduces capsule retention by approximately 50 percent.

TABLE 3

The Effect of Ethanol Pre-washing of Gelatin Capsules on the Retention of rhDNase Emptied at a flow rate of 30 liters per minute with a 4 liter inspiration.

Mean of 5×10 mg capsules 1:9 blend formulation of rhDNase

TABLE 3

The Effect of Ethanol Pre-washing of Gelatin Capsules on the Retention of rhDNase
Emptied at a flow rate of 30 liters per minute with a 4 liter inspiration.
Mean of 5 × 10 mg capsules containing 1:9 blend formulation of rhDNase

| Formulation/capsules | Capsule Retention of rhDNase (mg/capsule)[1] |
|---|---|
| 1:9/unwashed capsules | 0.34 |
| 1:9/washed capsules | 0.14 |

[1]. Capsule retention was determined as bulk UV assay of 5 emptied capsules (280 nm).

Table 3 below presents the performance data, as determined by MSLI, for washed and un-washed capsules. It can clearly be seen that MSLI experiments confirm the decrease in capsule retention and show that a greater amount of respirable particles are delivered from the DPI device.

TABLE 4

Comparison of the Performance of "Washed" and "Un-washed" Capsules
MSLI @ 60 liters per minute, mean of 3 determination each using 10 × 10 mg capsules containing 1:9 blend formulation of rhDNase

| Capsule | Respirable Dose of rhDNase[1] (mg) |
| --- | --- |
| Un-Washed | 0.16 |
| Washed | 0.21 |

[1]. Respirable dose refers to the fraction of the nominal dose less than 6.3 μm in diameter. It is a measure of that fraction of the nominal dose with the potential to penetrate and be deposited in the lower airways.

C. Conclusions

Washing hard gelatin capsules to remove the mould release coating is an effective means of reducing drug retention in capsules and increasing the delivered dose of medication. The data clearly show that for low dosage drugs, this would be an effective way of significantly reducing the nominal dose needed to ensure an adequate dose reaching the patient.

EXAMPLE 3

Capsule Dusting

Capsule dusting experiments were carried out using micronized lactose, mannitol and sodium chloride as dusting agents. rhDNase blends, "standard" capsules, capsule emptying and multistage impinger were as described for Example 1.

A. Capsule Dusting

An aliquot of dusting excipient was placed inside each capsule and without piercing the capsule a "mock" emptying test was carried out (see below). After the emptying test the capsules were opened and the excess excipient was removed by tapping the capsule. The formulation was then weighed into the capsule prior to the capsule retention experiments.

B. Capsule Emptying

Capsule emptying was investigated by loading 10 mg nominal doses of the rhDNase formulation into fresh capsules and then carrying out an emptying test. The test consisted of piercing the gelatin capsules, placing them in a DPI and then drawing 4 liters of air at a flow rate of 30 liters per minute through the DPI. Drug retention in capsule was assessed by washing "emptied" capsules and assaying the retained rhDNase using UV spectroscopy (280 nm). The washings from "emptied" capsules were read against a blank of the washings from "unused" capsules. The contact time between the purified (Milli-Q) water and the capsule bodies was minimized in order to reduce assay interference from the gelatin. Blank runs indicated that the interference from the capsule shells was minimal and acceptably corrected for by using the unused washings as the solution blank.

C. Results

Table 4 below presents the emptying data obtained during the capsule dusting experiments.

TABLE 5

The Effect of Capsule Dusting on Capsule Retention of rhDNase Emptied at a flow rate of 30 liters per minute with a 4 liter inspiration.
Mean of 5 × 10 mg capsules containing 1:9 pure rhDNase:carrier blend.

| Dusting Excipient[1] | Capsule Retention of rhDNase (mg/Capsule)[2] |
| --- | --- |
| None | 0.34 |
| Micronized Lactose | 0.13 |
| Micronized Mannitol | 0.24 |
| Spray dried Mannitol | 0.35 |
| Micronized Sodium Chloride | 0.24 |

[1]. Capsules were dusted by placing powder in the capsule and carrying out a mock emptying experiment without piercing the capsules. Excess powder was then emptied before the capsules were loaded with the 1:9 formulation.
[2]. Capsule retention was determined as bulk UV assay of 5 emptied capsules (280 nm).

D. Conclusions

Capsule dusting with an appropriate "fine" excipient can significantly reduce capsule retention and should therefore result in enhanced delivery of drug from a DPI device in patients.

We claim:

1. A method of treating a two part hard gelatin, cellulose or plastic capsule used for storing a pharmaceutical powder which is administered to a patient in the form of an aerosol, wherein the capsule has mould-release lubricant which reduces friction between a mould and the capsule coated on the inner surface thereof said method consisting essentially of the following steps performed sequentially:

(a) exposing the lubricant-coated inner surface of the capsule to a solvent which is different from the lubricant, wherein the solvent dissolves the lubricant but not the capsule, and (b) inserting the pharmaceutical powder in the capsule.

2. The method of claim 1 wherein the lubricant comprises silicone oil, sodium lauryl sulfate, magnesium lauryl sulfate, fatty acid, stearic acid, lauric acid, magnesium stearate, aluminum stearate, calcium stearate, boric acid, vegetable oil, mineral oil, paraffin, phospholipid, lecithin, polyethylene glycol, sodium benzoate, or mixtures thereof.

3. The method of claim 2 wherein the solvent is volatile and bactericidal.

4. The method of claim 2 wherein the solvent comprises benzene, hexanol, water, alcohol, methanol, ethanol, propanol, isopropanol, propylalcohol, ether, detergent solution, soap solution, chloroform, carbontetrachloride, or mixtures thereof.

5. The method of claim 4 wherein the solvent is an alcohol.

6. The method of claim S wherein the alcohol is dissolved in water.

7. The method of claim 1 wherein the lubricant is an oil.

8. The method of claim 1 wherein the pharmaceutical powder comprises particles having an average diameter of about 0.1 to 20 micrometers.

9. The method of claim 1 wherein the pharmaceutical powder comprises a pharmaceutical polypeptide.

10. The method of claim 1 wherein the pharmaceutical powder comprises a pharmaceutical compound and a pharmaceutically acceptable carrier.

11. A capsule which has been treated according to claim 1.

12. The capsule of claim 11 containing a pharmaceutical powder therein.

13. A method of treating a two part hard gelatin, cellulose or plastic capsule used for storing a pharmaceutical powder which is administered to a patient in the form of an aerosol, wherein the capsule has mould-release lubricant which reduces friction between a mould and the capsule coated on the inner surface thereof said method consisting essentially of the following steps performed sequentially:

(a) dusting the lubricant-coated inner surface of the capsule with a pharmaceutically acceptable dusting agent which is different from the pharmaceutical powder and has an average particle size of between about 0.1 to 20 micrometers, wherein the dusting agent adsorbs the lubricant, and (b) inserting the pharmaceutical powder in the capsule.

14. The method of claim 13 wherein the dusting agent is selected from the group consisting of: a sugar, a monosaccharide, a disaccharide, a polysaccharide, arabinose, xylitol, dextrose, maltose, sucrose, dextrin, dextran, lactose, mannitol, glucose, fructose, sorbitol, trehalose, a salt, sodium chloride, potassium chloride, starch, cellulose, methylcellulose and polyethylene glycol.

15. The method of claim 14 wherein the dusting agent has been micronized or spray dried.

16. The method of claim 15 wherein the dusting agent is micronized lactose.

17. A capsule which has been treated according to claim 13.

* * * * *